United States Patent
Shang

(10) Patent No.: US 10,632,322 B2
(45) Date of Patent: Apr. 28, 2020

(54) MEMORY METAL OPTICAL FIBER PUNCTURE NEEDLE TUBING

(71) Applicant: Hua Shang, Jiangsu (CN)

(72) Inventor: Hua Shang, Jiangsu (CN)

(*) Notice: Subject to any disclaimer, the term of this patent is extended or adjusted under 35 U.S.C. 154(b) by 0 days.

(21) Appl. No.: 16/373,771

(22) Filed: Apr. 3, 2019

(65) Prior Publication Data

US 2020/0030624 A1    Jan. 30, 2020

Related U.S. Application Data

(63) Continuation of application No. PCT/CN2018/097462, filed on Jul. 27, 2018.

(51) Int. Cl.
| | | |
|---|---|---|
| *A61N 5/00* | (2006.01) | |
| *A61N 5/06* | (2006.01) | |
| *G02B 6/26* | (2006.01) | |
| *A61B 17/34* | (2006.01) | |
| *A61B 17/00* | (2006.01) | |

(52) U.S. Cl.
CPC ........ *A61N 5/0601* (2013.01); *A61B 17/3417* (2013.01); *A61N 5/062* (2013.01); *G02B 6/262* (2013.01); *A61B 2017/00867* (2013.01); *A61B 2017/346* (2013.01); *A61N 2005/063* (2013.01); *A61N 2005/0612* (2013.01)

(58) Field of Classification Search
CPC .. A61N 5/0601; A61N 5/0603; A61N 5/0612; A61N 5/062; A61N 2017/320733; A61N 17/320741; A61N 17/32053; A61N 17/3207; A61N 17/3417; A61B 10/0275; A61B 10/0293

See application file for complete search history.

(56) References Cited

U.S. PATENT DOCUMENTS

| | | | | |
|---|---|---|---|---|
| 4,662,808 A | * | 5/1987 | Camilleri | F16B 13/12 411/340 |
| 5,674,242 A | * | 10/1997 | Phan | A61F 2/07 606/195 |
| 2007/0093780 A1 | * | 4/2007 | Kugler | A61B 17/221 604/510 |
| 2007/0255366 A1 | * | 11/2007 | Gerber | A61N 1/0558 607/116 |

(Continued)

FOREIGN PATENT DOCUMENTS

JP    2000354626 A * 12/2000

*Primary Examiner* — Michael W Kahelin
*Assistant Examiner* — Sana Sahand
(74) *Attorney, Agent, or Firm* — Hauptman Ham, LLP

(57) ABSTRACT

A memory metal optical fiber puncture needle tubing includes an optical fiber, a body tube, a metal casing and a split-shaped needle. The optical fiber has a body portion and a head portion. The head portion has a cylindrical head portion and a tapered head portion. The body tube surrounds the body portion. The metal casing is wrapped around the cylindrical head portion. The split-shaped needle is made of memory metal surrounding a periphery of the tapered head portion. The split-shaped needle has a plurality of tapered petals. When a temperature of the split-shaped needle is T0, the tapered petals are in a closed state such that the split-shaped needle is conical. When the temperature of the split-shaped needle is T1, the tapered petals are in an opened state such that the tapered head portion of the optical fiber is exposed.

11 Claims, 7 Drawing Sheets

(56) References Cited

U.S. PATENT DOCUMENTS

| | | | |
|---|---|---|---|
| 2009/0304576 A1* | 12/2009 | Warren | A61K 9/0024 424/1.11 |
| 2010/0081877 A1* | 4/2010 | Vakharia | A61B 1/00135 600/121 |
| 2012/0095532 A1* | 4/2012 | Gertz | A61N 5/0603 607/88 |
| 2015/0012072 A1* | 1/2015 | Johnson | A61N 5/0601 607/92 |
| 2018/0317949 A1* | 11/2018 | Lenker | A61M 25/09025 |
| 2019/0099195 A1* | 4/2019 | Carroll | A61B 17/32002 |
| 2019/0160306 A1* | 5/2019 | Rabiner | A61M 25/10 |

* cited by examiner

MEMORY METAL OPTICAL FIBER PUNCTURE NEEDLE TUBING

PRIORITY CLAIM

The present application is a continuing application of PCT Patent Application No. PCT/CN2018/097462, filed Jul. 27, 2018, which is incorporated herein by reference in its entirety.

TECHNICAL FIELD

The present disclosure relates to the technical field of medical instruments, in particular to a memory metal optical fiber puncture needle tubing.

BACKGROUND

Photodynamic Therapy (PDT) is a new technology for the diagnosis and treatment of diseases by using the photodynamic effect. This therapy is based on the photodynamic effect. This is a photosensitization reaction with biological effects in which oxygen molecule is involved. It comprises the following processes: the photosensitizer absorbed by a tissue is excited by the irradiation of a specific wavelength of laser; and then the excited state of the photosensitizer transfers energy to the oxygen in the surrounding environment, to generate a highly active singlet oxygen; singlet oxygen and adjacent biomacromolecules occur oxidation reaction, and thus produce cytotoxicity, which in turn leads to cell damage and even death. Compared with traditional therapies, photodynamic therapy has the advantages of less trauma, good targeting, no drug resistance and side effects. However, since photodynamic therapy mainly uses in the range of more than 600 nm wavelength in the red light region, the light in this region will be lost due to the absorption in a human body. Generally, only the light having the wavelength in few millimeters to several tens of millimeters can be transmitted. For some tumors deep in the body, photodynamic therapy is ineffective. With the aid of optical fiber, endoscopes, and other interventional techniques, the laser can be directed into the deep of body for treatment, avoiding the trauma and pain of surgery such as thoracotomy and laparotomy. Currently, light can be introduced into the body by a puncture needle comprising optical fiber, but since light needs to be led out of fiber optics, it is necessary for the tip of needle to have a hole with a sufficient size to allow light to pass out, increasing the diameter of the needle. In order to overcome the resistance during puncturing, the optical fiber is wrapped by a hard metal material. Therefore, the needle tubing is thicker. During the process for puncturing, a large pressure is required to perform the puncturing, which is likely to cause a larger trauma and damage to the normal vascular tissue, and bleeding. Therefore, for this series of problems, the present disclosure has developed a memory metal optical fiber puncture needle tubing.

SUMMARY

In view of the above, an object of the present disclosure is to provide a memory metal optical fiber puncture needle tubing, so as to solve defects in the prior art.

The object of the present disclosure can be achieved by the following technical solutions.

A memory metal optical fiber puncture needle tubing is provided. The puncture needle tubing comprises an optical fiber comprising a body portion and a head portion, in which the head portion comprises a cylindrical head and a tapered head having a tapered diameter formed by a taper method; the periphery of the body portion is wrapped with a body tube, the cylindrical head is wrapped with a metal casing, and the periphery of the tapered head is wrapped with a split-shaped needle made of memory metal; the metal casing is fixedly connected with the split-shaped needle, and the split-shaped needle is composed of a plurality of tapered petals;

when the temperature is T0, each of tapered petals in the split-shaped needle made of memory metal is closed, and the split-shaped needle after closing exhibits a conical structure, and after closing, the split-shaped needle is just wrapped around the tapered head of optical fiber; when the temperature is T1, each of tapered petals in the split-shaped needle made of memory metal is opened, and the tapered head of the optical fiber is exposed to enable light to direct irradiate onto the tumor.

Further, the metal casing is provided with an inverted-tooth structure, so as to have a smaller resistance when advancing, and have a larger resistance when retreating, thereby effectively reducing the thrust required for puncturing.

Further, the body tube is a spiral tube comprising a plurality of spiral coils, and the spiral tube is a spiral structure having spiral kerfs formed by laser cutting; the length of the body tube is 1 to 2 m.

Further, the metal casing is tightly wrapped around the periphery of the body portion of the optical fiber, to integrally connect the optical fiber with the metal casing; the metal casing is a spiral metal casing or has a structure that at least one inverted kerf is provided on the outer structure thereof; if it is the spiral metal casing, the metal casing is the spiral structure having spiral kerfs formed by laser cutting on a metal tube, so that it has a certain strength while increasing a certain flexibility.

Further, the tapered petals have the same curvature at each point and are formed by arc-shaped surfaces.

Further, all of the tapered petals are identical in terms of shape and size.

Further, the metal sheet for making the metal casing has an inverted-tooth structure with a thickness of the front end smaller than that of the rear end, to make the optical fiber puncture needle advancing easier and retreating tough.

Further, an end of the optical fiber puncture needle tubing left outside the body is connected with a drive device capable of vibrating backwards and forwards, in order to apply a forward force to the optical fiber puncture needle while vibrating.

Further, the drive device is a sonic vibration motor, has 10 μm to 500 μm of amplitude of vibration backwards and forwards, and 10 Hz to 1000 Hz of a vibration frequency.

Further, when no light is emitted from the optical fiber, the temperature of the split-shaped needle transmitted in the body is T0, and each of tapered petals in the split-shaped needle is closed together to form a needle shape or conical shape; when light is emitted from the optical fiber, the temperature of the split-shaped needle made of the memory metal raises to T1 after being exposed to light due to the thermal effect of the optical fiber, then each of tapered petals in the split-shaped needle is opened, and the tapered head of the optical fiber is exposed so that light on the optical fiber directly emits from the opened split-shaped needle.

Further, the body portion of the optical fiber is coated with a body coating for preventing light from being emitted from the side of the optical fiber; the tapered head of optical fiber has 1.45 to 1.55 of refractive index.

Further, the tapered head 2 has 7° to 25° of taper angle β.

Further, the temperature T0 is 37° C., and the temperature T1 is 50° C.; at the temperature T0, the split-shaped needle 5 is prefabricated into a closed shape; at a temperature T1, each of the tapered petals in the split-shaped needle is prefabricated into an opened shape; when puncturing, no light passes through the optical fiber, the temperature of the split-shaped needle is T0, and the transmission and puncture are achieved when closing; after reaching the predetermined site, the laser passes through the optical fiber, and the light on the tapered head of optical fiber irradiates to the memory metal, rising the temperature rises to T1, and thus opening the split-shaped needle.

Further, the length of the head portion is 7 to 10 mm, and the length of the split-shaped needle is 2.5 to 4 mm; the length of the metal casing is 4.5 to 6 mm.

Further, in the metal casing, the width a of the kerf is 0.1 to 0.2 mm, the width of the metal sheet for making the spiral structure of the metal casing is 0.2 to 1 mm; in the inverted-tooth structure, the front end of the metal sheet is 50 to 70 µm of thickness, and the rear end of the metal sheet is 90 to 110 µm of thickness, and the difference in thickness between the front end and the rear end is 30-50 µm.

Further, the split-shaped needle comprises a tail end and a tip end, the width of the tapered petal is gradually decreased from the tail end to the tip end; when each of tapered petals is closed, the diameter of the tail end is larger than that of the tip end; the each tail end of the tapered petals are integrally connected to form an annular ring of the annular structure, and the annular ring is fixedly connected to the metal casing.

Further, when each of tapered petals is closed, two adjacent sides in the two adjacent tapered petals are closely abutted, and the split-shaped structure constitutes a fully enclosed conical structure.

Further, in the tapered petals, the sides for abutting or separating from the adjacent tapered petals are inclined faces, and all the inclined faces of the tapered petals are consistent in direction.

The present disclosure provides a memory metal optical fiber puncture needle tubing, the beneficial effects thereof is mainly in that: through the synergistic effect with various components, the puncture needle tubing can be transmitted fast in the long blood vessels, such as being able to smoothly pass through blood vessels up to 2 m long, and can achieve higher light emission efficiency and therapeutic effect, so that it has important application value and significance in the treatment of photodynamic tumors. In addition, the puncture needle tubing also can be applied in other fields, such as eliminating vascular obstructions or performing vascular puncture, etc.

The present disclosure subtly adopts the characteristics of the memory metal, and creatively combines with the moving temperature in the body and the thermal effect of light, etc. Thereby, in the transmission process, the present disclosure achieves that while protecting the optical fiber head, the closed split-shaped needle can also still perform the puncture. It is beneficial to across the blood vessels during moving, and thus is more practical. In addition, through the thermal effect of light, the split-shaped needle is opened during illumination, and the light in the optical fiber can be directly irradiated to the target site for treatment. Moreover, since a tapered head with a thinner diameter formed by the taper process is used as the head portion of the optical fiber, the effective irradiation rate of light is greatly improved, which is beneficial to the effective cooperation of light and photosensitizer, and reduces the waste of light or photosensitizer, thereby increasing the treatment effect and reducing costs. In addition, the present disclosure can emit a small amount of light from the kerfs of the metal casing, while the light is emitted from the tapered head, thereby assisting the tapered head to effectively treat the entire tumor and the like.

The present disclosure is designed with an inverted-tooth structure outside the metal casing, and is equipped with a vibration motor, so as to realize an effective transmission which is convenient to advance and not easy to retreat, and is favorable for moving smoothly in the blood vessels. Moreover, the specific structural arrangement of the metal casing not only ensures strength and flexibility thereof, but also has an important function that it can combine with the vibration motor to regularly undergo a slight deformation, which helps to advance in the blood vessels.

In summary, the present disclosure has good clinical application effect, strong practicability, and a potential value for promotion and application.

LIST OF REFERENCE SYMBOLS

Figure 1:
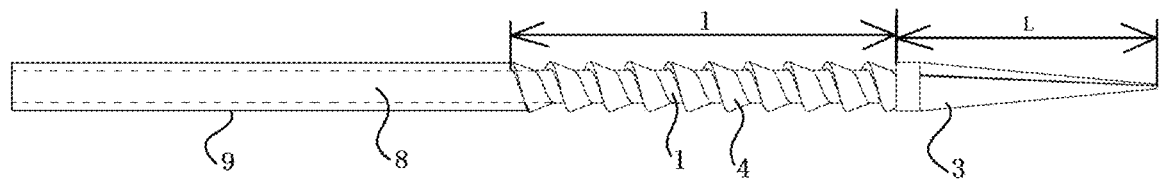
FIG. 1 is a schematic diagram illustrating the structure of the puncture needle tubing according to Example of the present disclosure, wherein the split-shaped needle is closed.

1 cylindrical head
2 tapered head
3 split-shaped needle
4 metal casing
8 body portion
9 body tube
31 tapered petal
32 annular ring
33 tip end
34 tail end
41 metal sheet
42 inverted-kerf
105 inclined face
106 polymer jacket
107 hydrophilic layer

DETAILED DESCRIPTION

Various examples of the present disclosure are described below for details. Apparently, the described examples are only a part of examples in the present disclosure, rather than all of them. While the following contains many specific implementation details, they should not be construed as limitations on the scope of any claims, but rather as descriptions to particular examples. Based on the examples provided by the disclosure, other examples obtained by those skilled in the art without creative efforts are encompassed in the scope of the disclosure.

Example 1

As shown in FIGS. 1-4, a memory metal optical fiber puncture needle tubing comprising an optical fiber is provided. The optical fiber comprises a body portion 8 and a head portion. The head portion comprises a cylindrical head 1 and a tapered head 2 having a tapered diameter formed by a taper method; one end of the cylindrical head 1 is fixedly or integrally connected to the body portion 8 or integrally shaped with the body portion 8, the other end is fixedly or integrally connected with the end having a larger diameter of the tapered head, or they are integrally shaped.

Figure 5:
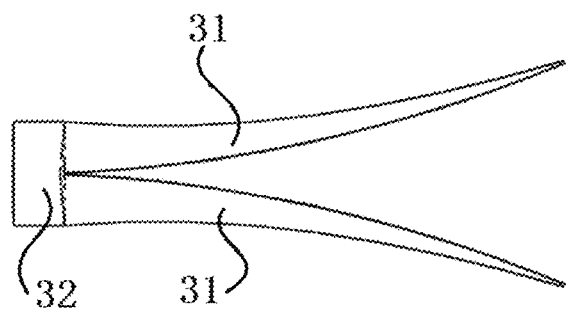
FIG. 5 is a schematic diagram illustrating the structure that the split-shaped needle according to Example of the present disclosure is opened.
Figure 6:
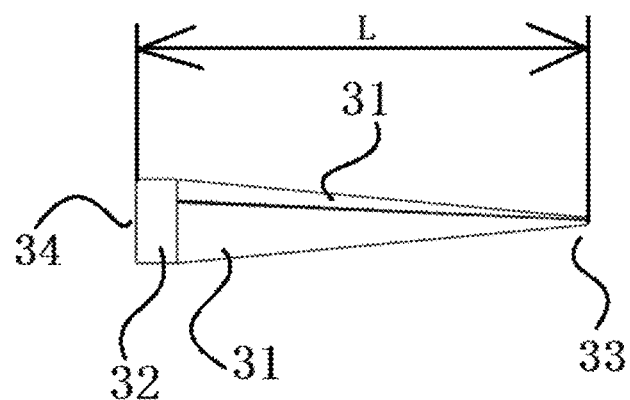
FIG. 6 is a schematic diagram illustrating the structure that the split-shaped needle according to Example of the present disclosure is closed.

The body portion 8 is wrapped with a body tube 9, and the cylindrical head 1 is wrapped with a metal casing 4. The metal casing 4 wraps around the periphery of the cylindrical head 1 tightly, to integrate the cylindrical head 1 of the optical fiber with the metal casing 4. The periphery of tapered head 2 is wrapped with a split-shaped needle 3 made of memory metal. The split-shaped needle can be deformed to the opened state, with the increasing of the temperature due to light illumination, so that light of the optical fiber can be emitted out. The metal casing 4 is fixedly connected to the tail end or the end having large diameter end of the split-shaped needle 3. The split-shaped needle 3 is composed of a plurality of tapered petals 31, as shown in FIG. 5-6. The head portion of optical fiber and the metal casing 4 outside the head portion and the split-shaped needle 3 can be collectively referred to as the head end.

Figure 2:
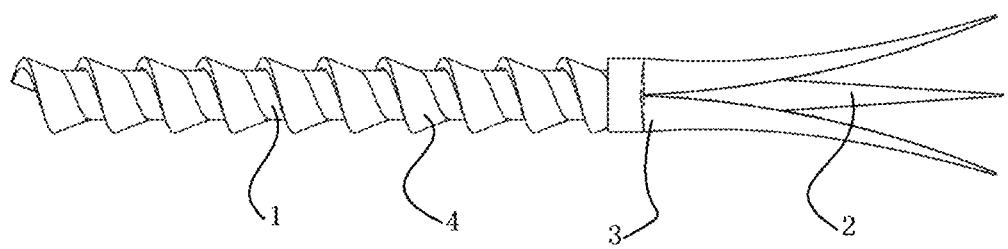
FIG. 2 is a schematic diagram illustrating the structure of head portion according to Example of the present disclosure, wherein the split-shaped needle is opened.
Figure 3:
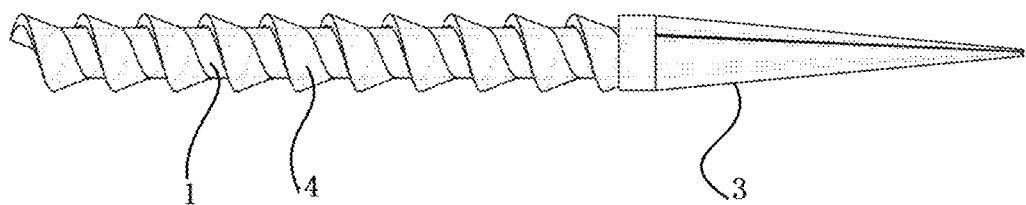
FIG. 3 is a schematic diagram illustrating the structure of head portion of optical fiber puncture needle tubing according to Example of the present disclosure.

When the temperature is T0, as shown in FIG. 2-3, each of tapered petals 31 in the split-shaped needle 3 made of memory metal is closed, and the split-shaped needle 3 after closing exhibits a conical structure, and after closing, the split-shaped needle 3 is just wrapped around the tapered head 2 of optical fiber. The optical fiber is wrapped in the split-shaped structure to protect the optical fiber, and the conical split-shaped structure can conveniently move in the blood vessels during the passage through the blood vessels. In other words, the moving is smooth, i.e., when advancing, the resistance is smaller, while retreating, the resistance is larger.

When the temperature is T1, as shown in FIG. 1, each of tapered petals 31 in the split-shaped needle 3 made of memory metal is opened, and the tapered head 2 of optical fiber is exposed to enable light to direct irradiate onto the tumor.

The metal casing 4 is provided with an inverted-tooth structure, as shown in FIGS. 1-4. Such structure has a small resistance when advancing, and has a larger resistance when retreating, so that it can be puncturing in a progressive manner under a applied sight impact, and effectively reduce the force required for puncturing.

As a further preferred embodiment, as shown in FIGS. 1-4, the metal casing is a spiral metal casing. The metal casing has a spiral structure having spiral kerfs formed by laser cutting on a metal tube, so that it has a certain strength while increasing a certain flexibility.

As a further preferred embodiment, as shown in FIGS. 1-4 and 7, the metal sheet 41 for making the metal casing 4 has an inverted-tooth structure with a thickness of the front end smaller than that of the rear end, to make the optical fiber puncture needle advancing easier and retreating tough.

Figure 7:
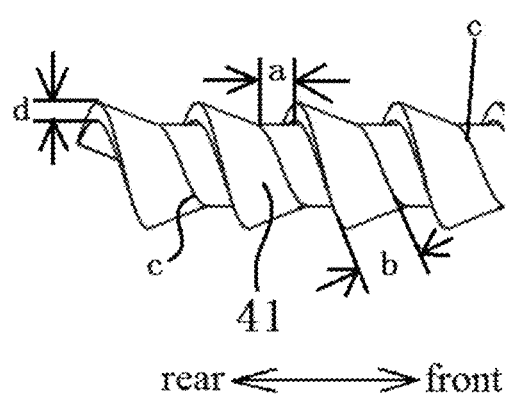
FIG. 7 is a schematic diagram illustrating the structure of a part of spiral metal casing according to Example of the present disclosure.

More preferably, as shown in FIG. 7, as the thickness c of the front end of the metal sheet is too thin, the thickness thereof is not easily indicated in this figure, so that only the position of c is indicated, and the thickness relationship is not provided. In the inverted-tooth structure of the metal casing 4, i.e., the structure in which the thickness of the front end of the metal sheet for making the metal casing is smaller than that of the rear end, the thickness c of the front end of the metal sheet is 50 to 70 µm, the thickness d of the rear end of the metal sheet is 90 to 110 µm, and the difference in thickness between the front end and the rear end is 30 to 50 µm. Controlling thickness is quite important for effective and smooth transmission and advancement. If the thickness difference is too large, it either needs to increase the outer diameter of the metal casing, or needs to reduce the inner diameter of the metal casing, which has a greater influence on the overall puncture needle tubing. In addition, if the thickness difference is too large, the thickness of the back side of the metal sheet will be increased greatly, which in turn increases the resistance during advancing. Moreover, for the small or fine blood vessels, it will increase the degree of damage to the inner wall of the blood vessels. If the thickness difference is too small, it cannot play the role of assisting advancement and preventing retreating.

More preferably, in the metal casing 4, as shown in FIG. 7, the width a of the kerf is 0.1 to 0.2 mm, such as 0.1 mm, 0.15 mm, 0.2 mm, etc., and the width b of the metal sheet for making the spiral structure is 0.2 to 1 mm, such as 0.2 mm, 0.4 mm, 0.6 mm, 0.8 mm, 1 mm, etc. The values of the kerf width a and the spiral sheet width b and the cooperation thereof directly affect the ability to pass through the blood vessels and the smoothness of passing through the blood vessels, and even affect the puncture strength from one blood vessel to another. Width a and width b that are too wider and too narrow will affect its flexibility and strength. If the strength is too high, it cannot pass through the curvature of the blood vessel, and the damage to the inner wall of the blood vessel will be serious; if the flexibility is too high, it cannot pass through the blood vessel having a longer length, especially, when the length of blood vessels to be passed through is within 1 m, it may pass through blood vessels relatively easier, while when the length beyond 1 m, it will be difficult for the structure to pass through such blood vessels. In addition, it is not easy for the user to control the strength and direction through the handheld end. In addition, when piercing and entering another blood vessel from one blood vessel, a lower strength will lead to the inability to pierce the blood vessel. Therefore, when the strength is too high or the flexibility is too high, the device cannot reach blood vessels or organs buried inside the body in a certain depth, such as liver tumors. A good effect can only be achieved upon the suitable width a and suitable width b.

As a further preferred embodiment, an end of the optical fiber puncture needle tubing left outside the body is connected with a drive device capable of vibrating backwards and forwards, in order to apply a forward force to the optical fiber puncture needle tubing while vibrating.

Preferably, the drive device is a sonic vibration motor, has 10 μm to 500 μm of amplitude of vibration backwards and forwards, and 10 Hz to 1000 Hz of a vibration frequency.

Figure 8:
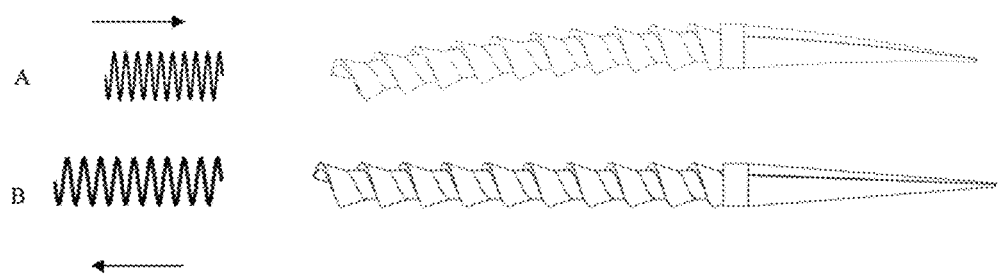
FIG. 8 is a schematic diagram illustrating the structural deformation of the optical fiber puncture needle tubing according to Example of the present disclosure under the drive of the vibration motor.

For example, when puncturing, the puncture needle tubing is connected to the sonic vibration motor which has 100 Hz of the vibration frequency and 50 μm of the vibration amplitude. As shown in FIG. 8, when the puncture needle tubing is vibrating, the whole structure of the puncture needle tubing is deformed to conduct the vibration. The puncture needle is slightly deformed when it is vibrated forward. As shown at A, the deformation includes the bending of the puncture needle tubing and the shrinkage in the pitch of the metal casing 4. Such elastic deformation causes the tip of the needle to move forward and overcome the resistance, so as to achieve the forward puncture. When it is vibrated backward, as shown at B, since the metal casing 4 has the inverted-tooth structure, the friction is much greater than the forward movement, the puncture needle tubing is pulled and moved forward as whole, but the tip of the needle may stay still. The puncture needle tubing continues to puncture forward under the effect of multiple vibrations while applying additional force. This means of puncturing requires less force than the conventional puncture needle, thus allowing the optical fiber puncture needle to be finer and softer, and at the same time capable of completing the puncture effect.

As a further preferred embodiment, when no light is emitted from the optical fiber, i.e., a laser is connected to the end of the optical fiber puncture needle tubing left outside the body and the laser is not turned on, the temperature of the split-shaped needle transmitted in the body is T0, each of tapered petals in the split-shaped needles is closed to form a needle-shaped structure or a conical structure. When the optical fiber emits light, i.e., the laser connected to the optical fiber is turned on to transmit the light to the optical fiber, after being exposed to light, that is, the light is emitted by the tapered optical fiber and irradiated on the memory metal, the temperature of the split-shaped needle 3 made of the memory metal is gradually increased to T1 due to the thermal effect of the optical fiber. Then, each of tapered petals in the split-shaped needle is opened, i.e., the outward prefabricated deformation is generated to exhibit the opened state. Light exits through the opening, that is, the tapered head of the optical fiber is exposed to enable light to direct emit from the opened split-shaped needle.

Figure 9:
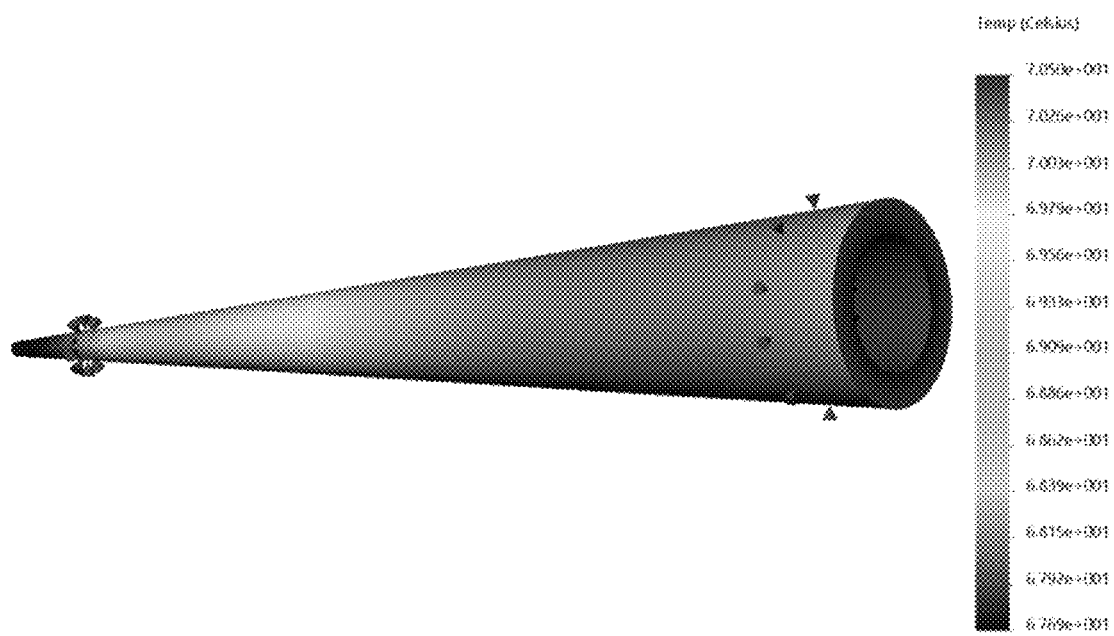
FIG. 9 is a schematic diagram of temperature distribution when the split-shaped needle according to Example of the present disclosure is irradiated with light.

The temperature T0 may be 37° C., and the temperature T1 may be 50° C. For example, at the temperature T0 (for example, 37° C.), the split-shaped needle 3 is prefabricated into the closed shape, and at the temperature T1 (for example, 50° C.), the split-shaped needle 3 is prefabricated into the opened shape. When puncturing in the body, no light passes through the optical fiber, and the temperature of the split-shaped needle 3 in the head portion is the body temperature T0 (37° C.). The transmission and puncturing can be realized as the split-shaped needle 3 is closed. After reaching a predetermined site, a 100 mW laser with a wavelength of 650 nm passes through the optical fiber, and radiates to the split-shaped needle 3 made of a memory metal through the tapered head of the optical fiber. As shown in FIG. 9, it shows the outside of the puncture needle having a 500 W/(m²·K) convection heat conduction (typical heat dissipation rate of liquid convection), in which the temperature of the needle can be raised to 70.5° C. under a 100 mW laser, and when exceeding T1 temperature (50° C.), the needle is deformed to the opened state.

As a further preferred embodiment, the tapered petals 31 have the same curvature at each point and are formed by arc-shaped surfaces, so that the overall moving effect is better.

All of the tapered petals 31 are identical in terms of shape and size, so that the forces distributed on the tapered petals 31 are more uniform, and the strength thereof is greater.

The split-shaped structure comprises 2 to 5 tapered petals, preferably 2 tapered petals or 3 tapered petals; too many or too few tapered petals will lead to insufficient strength.

As a further preferred embodiment, the length of the head portion is 7 to 10 mm, in which the length L of the split-shaped needle 3 is 2.5 to 4 mm, such as 3 mm. The length of the metal casing 4 or the cylindrical head 1 is 4.5 to 6 mm, such as 5 mm; as shown in FIGS. 1 and 6. The thickness of the split-shaped needle 3 or the tapered petals 31 is 0.06 to 0.12 mm. When it is closed, it is just wrapped around the outside of the tapered head 2. Preferably, there is no gap between the tapered head 2 and the split-shaped needle. In addition, the tapered head 2 has an effect of assisting the improvement of strength of the split-shaped needle 3; and it can combine with the tapered petals 31 having a certain thickness, to facilitate the transmission and piercing of the puncture needle tubing, which brings out a synergistic effect.

As a further preferred embodiment, the diameter at the foremost end of the tapered head is 10 to 50 μm, such as 20 μm, 30 μm, 40 μm.

As a further preferred embodiment, the length of the body tube 9 is 1 to 2 m, such as 1.8 m. The length of the body tube 9 is the same as that of the body portion 8 of the optical fiber. The body tube is tightly wrapped around the body portion 8 of the optical fiber, so that they can be integrated together for easy transmission.

The body portion 8 and the cylindrical head 1 of the optical fiber may have a diameter of 400 μm, which may be a quartz fiber, and the metal casing 4 and the body tube 9 may have an outer diameter of 600 μm and an inner diameter of 400 μm.

As a further preferred embodiment, the split-shaped needle 3 includes a tail end 34 and a tip end 33, as shown in FIG. 6. The tapered petals 31 is gradually decreased from the tail end to the tip end. When each of tapered petals 31 is closed, the diameter of the tail end 31 is larger than that of the tip end 33; the each tail end of the tapered petals are integrally connected to form an annular ring 32 of the annular structure, and the annular ring 32 is fixedly connected to the metal casing 4.

As a further preferred embodiment, when each of tapered petals 31 is closed, two adjacent sides in the two adjacent tapered petals 31 are closely abutted, and the split-shaped structure constitutes a fully enclosed conical structure, thereby better protecting the tapered head of the optical fiber. As it the tapered head is polluted during the transmission process, it will affect the irradiation rate of light, and thus affects the action of the photosensitizer on the tumor site.

In this example, when using, the end of the head is first pierced into the blood vessel and then transmitted in the blood vessel, and the end of the puncture needle left outside of the body can be connected to the vibration motor, so as to assist the puncture needle reaching a predetermined site, such as a tumor in the body (e.g., liver tumors) via the blood vessel.

Example 2

On the basis of example 1, the body tube 9 is a spiral tube containing a plurality of spiral coils, and the spiral tube has spiral kerfs formed by laser cutting.

Figure 12:
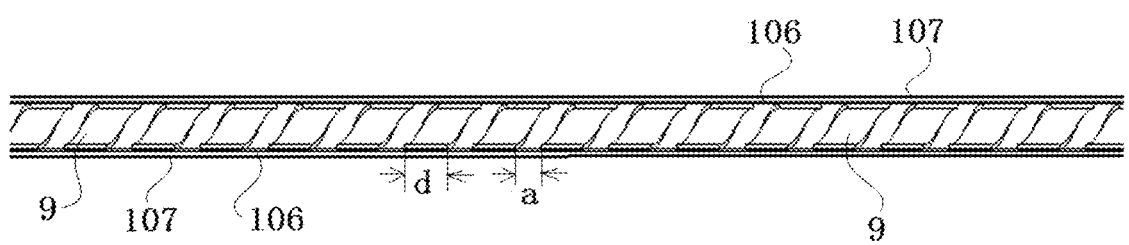
FIG. 12 is a section diagram of the structure of the body tube according to Example 3 of the present disclosure (viewing from the center to the outside)

As shown in FIG. 12, it shows a cross-section of the body tube, viewing from center to the outside. In the body tube 9, the width a of the kerf is 0.02 to 0.2 mm, such as 0.05 mm, 0.1 mm 0.15 mm, etc., the width d of the spiral sheet for making the spiral structure in the body tube 9 is 0.5 to 3 mm, such as 1 mm, and the thickness thereof is 0.05 to 0.1 mm, such as 0.08 mm. The length of the body tube 9 is nearly 2 m, and usually 1 to 1.8 m thereof will enter the human body. In addition, the human blood vessels have different thicknesses and a certain degree of curvature. As the blood vessels to be passed through are so long, and the environment are so specific, there are highly requirement for its strength and flexibility. The values of the kerf width a and the spiral sheet width d and the cooperation thereof directly affect the ability to pass through the blood vessels and the smoothness of passing through the blood vessels, and even affect the strength of the head portion puncturing the tumor blood vessel walls. The width a and width d that are too wider or too narrow will affect the flexibility and strength. A good effect can only be achieved upon the suitable width a and suitable width d.

The body tube 9 is made by a biomedical metal material including but not limited to one of stainless steel, synthetic fiber, carbon fiber, titanium alloy, gold, silver, etc., preferably stainless steel. As a whole, the body tube is composed of at one winding wire (may be two or more winding wires) wrapped around the periphery of body portion 8 of the optical fiber and made of the stainless steel actually.

Figures 13, 14:
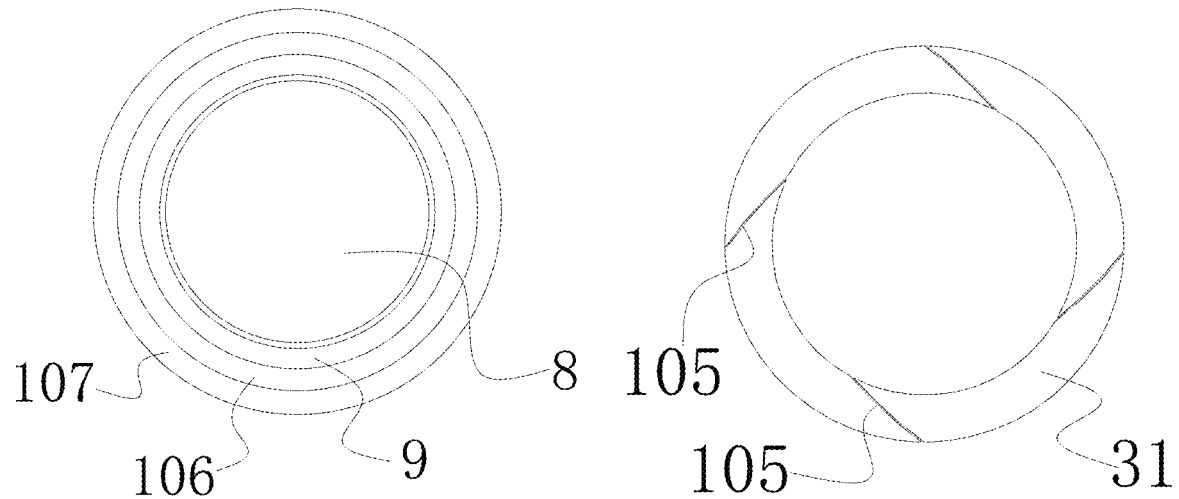
FIG. 13 is a cross-sectional diagram illustrating the body tube wrapped outside the body portion according to Example of the present disclosure.
FIG. 14 shows the cross section that the split-shaped needle according to Example of the present disclosure is closed.

As shown in FIGS. 12-13, a polymer jacket 106 is provided on the outside of the body tube 9, to increase the sealing of the guide tube and reduce the resistance; the material of polymer jacket 106 may be polyamide or polypropylene, etc., and other polymers may be acceptable. A hydrophilic coating 107 is provided on the outside of the polymer jacket 106, to increase blood compatibility. The hydrophilic coating 107 is made of a chemically stable material including but not limited to, polytetrafluoroethylene, silicone rubber, polyethylene, polyvinyl chloride, fluorocarbon polymers, and polyurethane. The hydrophilic coating is applied to reduce the resistance in the blood vessel and to pass through the long blood vessels with complex internal environment.

The hydrophilic coating 107 in this example may be replaced with a hydrophobic coating.

Example 3

Figure 10:
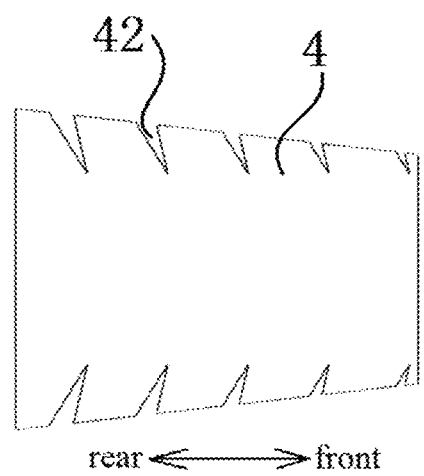
FIG. 10 is a schematic structural diagram of the outer surface of the metal casing according to Example 3 of the present disclosure.
Figure 11:
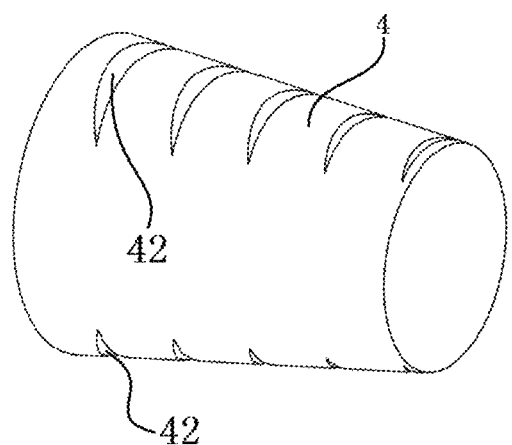
FIG. 11 is a schematic structural diagram of the outer surface of the metal casing according to Example 3 of the present disclosure.

The metal casing 4 of the example 2 may also have a structure in which a plurality of inverted kerfs 42 are provided on the outer surface thereof, as shown in FIGS. 10-11, i.e., is, wedge-shaped inverted kerfs 42 formed on the outer surface of the metal tube by laser cutting. That is, the inverted kerfs 42 is inclined rearward. As shown in FIG. 10, the width of the inverted kerfs 42 is from one end of the outer side surface to one end near the inner side surface, and the thickness thereof is gradually decreased.

Preferably, the metal casing 4 in this example may have a structure in which the diameter is gradually decreased from the tail end to the front end, that is, from the back to the front, which is convenient to advance, as shown in FIGS. 10-11.

Example 4

Figure 4:
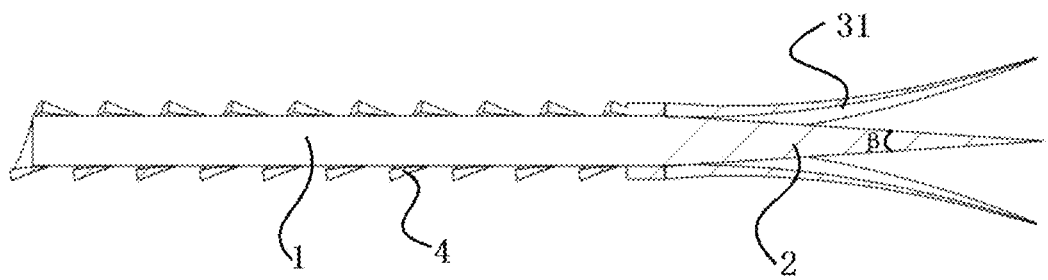
FIG. 4 is a cross-sectional diagram illustrating the structure of head portion of optical fiber puncture needle tubing according to Example of the present disclosure.
Figure 16:
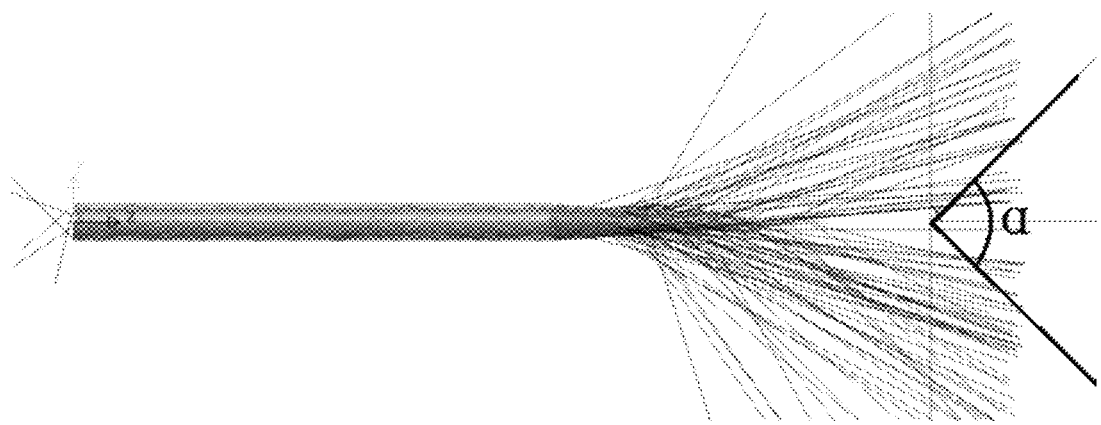
FIG. 16 shows the emission range of light on the tapered head according to Example 4 of the present disclosure.

On the basis of example 2, the refractive index of the tapered head 2 of the optical fiber is 1.45 to 1.55, preferably 1.5, and the taper angle $\beta$ of the tapered head 2 is 7 to 25°, as shown in FIG. 4. This structure can substantially ensures that the light from the tapered head is in the range of 60-120°, the angle of which is indicated by $\alpha$ in FIG. 16. Specifically, through aoptical simulation, it can be known that if the cone angle $\beta$ is 22°, then the divergence angle $\alpha$ of the light is within 120°; and if the taper angle $\beta$ is 7.6°, the divergence angle $\alpha$ of the light is within 60°. Therefore, when the taper angle $\beta$ of the taper head 2 is 7 to 25°, the light on the tapered head can be efficiently directed to the target position, such as a tumor containing a photosensitizer, so as to effectively utilize the light energy and greatly increase the light output rate.

The refractive index of the entire optical fiber may be 1.5. However, it is preferable that the outer surface of the body portion 8 of the optical fiber is coated with a cladding layer having a refractive index, such as 1.2, 1.3, etc., lower than that of the optical fiber, so that the light does not exit from the body portion 8 of the optical fiber, restricting the light. Therefore, light can only be emitted from the head portion. Thus, the light is directly irradiated onto the tumor containing the photosensitizer. The cladding layer may include silica as the main component, as specifically seen in the prior art.

Preferably, the optical fiber at the spiral casting, i.e., the cylindrical head 1 of the optical fiber at the kerfs of the spiral casting does not provide with a cladding layer or has a cladding layer with the refractive index slightly smaller than that of the cylindrical head 1 of the optical fiber. Then, a part of the light can be emitted from the kerfs of the spiral casting, so as to irradiate the other auxiliary parts. Therefore, the key part can be directly irradiated by the tapered head for effective irradiation, and meanwhile the cylindrical head 1 assists the irradiation of the epitaxial part, thereby realizing effective irradiation of the whole part to be irradiated. Irradiation of tumor tissue containing a photosensitizer can effectively increase the efficacy of the photosensitizer and ultimately increase its therapeutic effect.

Figure 17:
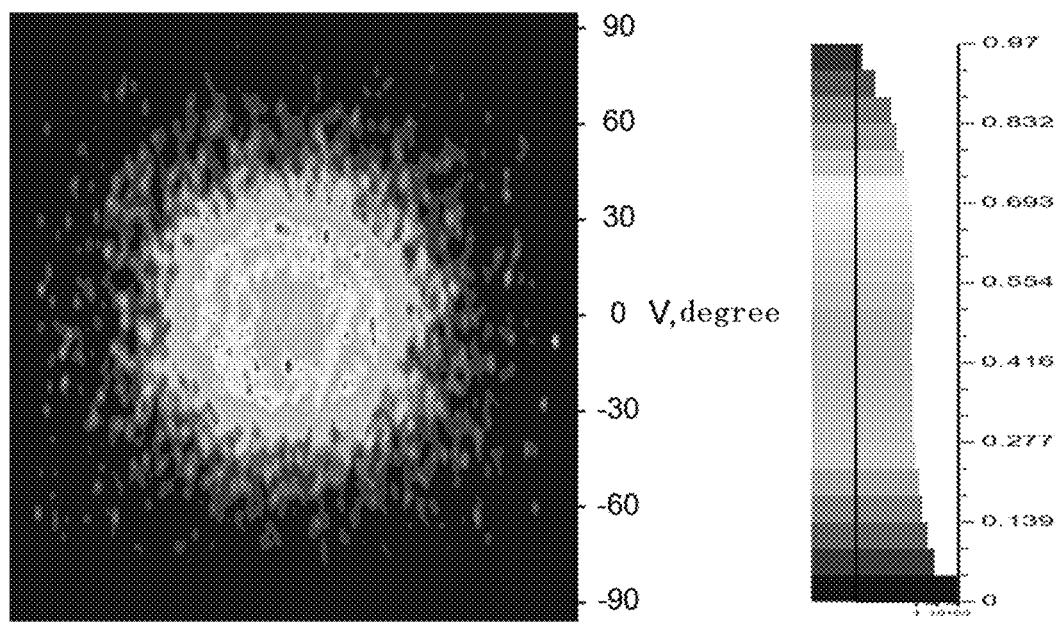
FIG. 17 shows the exit spot of the tapered head according to Example of the present disclosure.

In this example, FIG. 9 is a simulation of the optical transmission characteristics of the fiber optic taper. If the input optical fiber has a wavelength of 650 nm, when the input power is 1 W, the output rate of the light output from the optical fiber tapered head is 0.94 W, the output power is high. In addition, the divergence angle thereof is about 60°, which can effectively irradiate or treat the key parts. The shape of the spot is shown in FIG. 17.

Example 5

Figure 15:
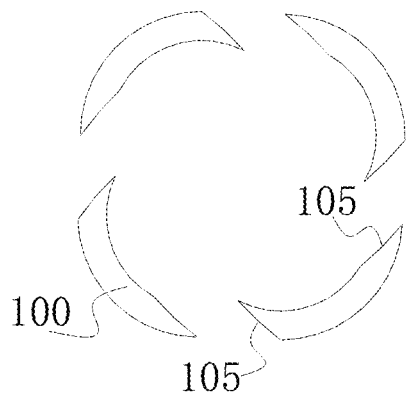
FIG. 15 shows the cross section that the split-shaped needle according to Example of the present disclosure is opened.

On the basis of any of the examples 1-4, as shown in FIGS. 14-15, in the tapered petals 31, the sides for abutting or separating from the adjacent tapered petals are inclined faces 105. That is, one tapered petal 31 has two sides, each of which has a beveled configuration. And all the inclined faces 105 of the tapered petals 31 are consistent in direction (i.e., in the clockwise or counterclockwise direction), which ensures that the two abutted inclined faces in two adjacent tapered petals can be just fitted together. That is, one is gradually inclined outward from the inside, while the other is inclined inward from the outside, and thus the two can be just fitted together, so that the inner and the outer surfaces after being fitted together are smooth arced surfaces.

The design of the beveled configuration means that the width of the sides is widened, so that the contact area is increased when the two adjacent tapered petals are abutting each other, and the bonding strength is greater between tapered petals 31 after the split-shaped needle 3 is closed, obtaining a better puncture effect of the needle-like structure. More importantly, since the sides are designed as inclined faces 105, the contact width is increased when the two adjacent tapered petals 31 are abutting each other, obtain a better sealing. Therefore, during the transmission in the blood vessels, it will not be make the optical fiber tapered head 2 in the inside infected, thus affecting the final light out.

This example shown in FIGS. 14-15 takes four tapered petals 31 as the example. But two or three tapered petals also can be used.

Example 6

On the basis of any of the examples 1-5, in the tapered petals 31, the side or inclined face 105 for abutting or separating from the adjacent tapered petals 31 is provided with a first flexible layer, to make the abutment strength between the tapered petals 31 more tight and the sealing therebetween better. The better sealing can prevent fluid contamination of the tapered head in the blood vessels better, while helping to increasing the strength of the closed split-shaped needle.

As a further preferred embodiment, the inner side surface of the tip end of the tapered petal is provided with a second flexible layer, to make when the split-shaped structure is closed, the abutment strength between the tapered petals more tight and the sealing therebetween better.

The first and second flexible layers may have a thickness of 0.005 to 0.04 mm, and the materials of the first and second flexible layers may be polytetrafluoroethylene, polyamide or polypropylene or the like.

Example 7

Use

The present discloses relates to the use of the memory metal fiber puncture needle tubing. the puncture needle tubing can be used in the moving in the blood vessels, the puncture of blood vessel wall, the piercing of an intravascular obstruction and the tumor photodynamic in the human body. The method for using the needle tubing comprising the following step in which the temperature T0 may be 37° C., the temperature T1 may be 50° C.;

(1) connecting a sonic vibration motor to the end left outside the body of the optical fiber puncture needle tubing; since the split-shaped needle is closed at the temperature T0 (such as 37° C.), the tapered head of the optical fiber is enclosed in the split-shaped needle, and then can puncture and move in the blood vessels;

(2) puncturing into a site to be punctured, such as a blockage or a blood vessel wall, when reached it;

(3) raising the temperature of the tapered head, when the optical fiber is connected to a laser to make the optical fiber emit light having a certain wavelength, such as a 100 mW laser with a wavelength of 650 nm; transferring the temperature to the split-shaped needle to raise the temperature thereof; opening the split-shaped needle when the temperature reaches T1 (such as, at 50° C.); the tapered head 2 is exposed to efficiently irradiate the portion to be irradiated.

If the optical fiber puncture needle tubing is used in photodynamic tumor treatment, if the interventional treatment is used for a liver tumor, the optical fiber puncture needle tubing pierces into the liver artery through the femoral artery, and finally enters the blood vessel of the liver tumor. Then, the laser is turned on, and the temperature is raised to open the split-shaped needle. Therefore, the light on the tapered head irradiates on the tumor which has been injected a photosensitive drug, so that the photosensitive drug (such as PHOTOFRINR) in the tumor produces singlet oxygen by the photochemical reaction, to cause necrosis and apoptosis of the tumor. Thereby the purpose of treating tumors can be achieved.

Thepresent disclosure has high light-emitting efficiency, good the light-emitting effect, and high treatment efficiency.

Example 8

In order to further study the practical effect of the optical fiber puncture needle tubing in this disclosure, the applicant has carried out the study from various aspects, such as the type and length of the blood vessels to be passed through, the passing time, the damage to the blood vessel, the strength of the tip, irradiation effect, treatment efficiency and and the accuracy, and so on.

Method:

taking the biopsy for liver tumor sampling as an example, through the Seldinger arterial puncture technique, under the guidance of radiography, at T0 temperature (such as 37° C.), the optical fiber puncture need tubing enters the hepatic artery through the femoral artery, then enters the hepatic blood vessels through the hepatic artery, and finally enters the tumor blood vessels, under the auxiliary of the vibration motor. Then, irradiation and treatment of tumor which has been added photosensitized are performed.

The length of the blood vessel passed through: 1.6 m.

The puncture needle tubing of examples 2, 4 to 5 are tested as the experimental groups 1 to 3 respectively.

Comparative Example 1: this comparative example is performed in the same manner as in example 2, except that the split-shaped needle is not used and the tapered head is exposed.

Comparative Example 2: this comparative example is performed in the same manner as in example 2, except that there is no the structure of tapered head, and the head portion of the optical fiber is the same as that of other parts.

Comparative Example 3: this comparative example is performed in the same manner as in example 2, except that there is no the structure of spiral casting 4 and inverted kerfs. That is, the tapered head directly connects with the body portion 8.

Comparative Example 4: this comparative example is performed in the same manner as in example 2, except that there is no tapered head and split-shaped needle. That is, the structure of the forefront of the puncture needle tubing is the cylindrical head 1 wrapped around the metal casing 4.

Comparative Example 5: the body tube of example 2 is changed to a spring.

Comparative Example 6: the spiral casting 4 of example 2 is changed to a spring.

The results of the above examples are summarized in the table below.

|  | Time to reach tumor blood vessels/min | output efficiency of the optical fiber | irradiation efficiency of the optical fiber | tip strength when puncturing/ |
| --- | --- | --- | --- | --- |
| Ex. 1 | 4-10 | 90% | 91% | 2.7N |
| Ex. 2 | 4-10 | 98% | 95% | 2.7N |
| Ex. 3 | 4-10 | 99% | 98% | 2.7N |
| Com. ex. 1 | 10-15 | 78% | 73% | 2.0N |
| Com. ex 2 | 4-10 | 90% | 68% | 2.5N |
| Com. ex 3 | 18-25 | 90% | 61% | 2.7N |
| Com. ex 4 | 20-35 | 82% | 53% | — |
| Com. ex 5 | 20-35 | 90% | 91% | 1.8N |
| Com. ex 6 | 15-30 | 90% | 91% | 1.9N |

In the above table, i) the time to reach the tumor blood vessels refers to the time required to move in the blood vessels before reaching the tumor tissue. ii) the output efficiency of the optical fiber refers to the percentage of light actually irradiated to the photosensitizer in the tumor and the light from the head portion theoretically irradiated to the photosensitizer in the tumor. iii) the irradiation efficiency of the optical fiber refers to the effective amount of light irradiated on the photosensitizer in the tumor, which is in positive ratio with the absorption efficiency of the photosensitizer; iv) the tip strength when puncturing refers to the force of the head of the puncture needle when puncturing the inner wall of the tumor blood vessels.

The results of the above experimental and comparative groups are explained as follows:

Example 1: the head portion of optical fiber has less light loss rate, and the light output rate is higher. That is, the light can basically be irradiated to the tumor (i.e., the photosensitizer) as required. However, since the divergence angle of the outgoing light is unstable, the effect of focusing light on a certain place is slightly inferior to that of example 2 or example 3.

Example 2: the structure can move in the blood vessels smoothly; and the outputting rate of light, the irradiation efficiency of the optical fiber, the puncture effect and the therapeutic effect are all better.

Example 3: the structure can move in the blood vessels smoothly; and the outputting rate of light, the irradiation efficiency of the optical fiber, the puncture effect and the therapeutic effect are all better.

Comparative Example 1: Because the tapered head is exposed, it has certain brittleness. Therefore, it needs to be careful when moving, and thus affects moving. Because the tapered head is exposed, the endovascular environment has a certain influence on it during the transmission process. In addition, some substances that can affect the refractive index and luminance of light may easy adhered to the tapered head during the process of moving, which leads to the light output efficiency of the optical fiber at the target position is low. Due to its low light output efficiency, it greatly affects the irradiation efficiency of the optical fiber. That is, the light irradiated on the photosensitized is decreased. The force at the tip when puncturing is decreased obviously.

Comparative Example 2: since there is no tapered head, the light is not highly directional. Therefore, some of the light cannot be effectively irradiated to the photosensitizer. In addition, the part needed to be irradiated fewer may be actually irradiated by more light, while the part that needs to key light may be actually irradiated less light. Therefore, the irradiating blindness is larger, the radiation efficiency of the optical fiber is low, thereby greatly influencing the efficiency of the treatment.

Comparative Example 3: as there is no inverted kerf structure, it will greatly assert the advance speed under the action of vibration motor. As the light is only emitted from the tapered head, the irradiation thereof is only spread over a small area, and specifically only can spread over some important parts; there is almost no light that can irradiate other auxiliary parts. Therefore, it greatly affects the irradiation efficiency, and thus greatly affects their treatment efficiency.

Comparative Example 4: i) since the structure of this comparative example is unable to puncture the blood vessels, it will affect moving thereof. Because the structure of this comparative example sometimes needs to pass through the blood vessel wall to enter and move in another blood vessel, it requires to cooperate in other ways which will greatly affect the total time of its moving. overall light output efficiency is low. In addition, the light is only emitted from the top surface of the optical fiber and the kerfs of the spiral casting, which leads to a great decrease in its illumination. As for comparative example 2, this comparative example also has a bigger blindness, which makes the light emitted cannot be used effectively. Therefore, the irradiation efficiency of the optical fiber is low, which greatly affects its treatment efficiency. due to the absence of the tip structure, the puncturing cannot be achieved.

Comparative Example 5: it is difficult to control the strength and direction, which greatly affects the total moving time. Since the strength thereof also cannot be controlled well, the puncturing effect at a certain point is significantly reduced.

Comparative Example 6: if the selected spring is consistent with the spiral casting in the strength, the flexibility and elasticity thereof are different from those of the spiral casting. In addition, the direction thereof is not easy to control, resulting in the tip shows less strength than the experimental groups on the whole. Moreover, when the spring cooperations with the vibration motor, its bending degree and the defamation effect are different from the present disclosure. Therefore, the advance speed under the action of the vibration motor is far less than the examples or experimental groups of the present disclosure.

Example 9

A rat tumor model was established. Rats having substantially the same tumor size were taken as the experimental object. In the control, only photosensitizer was applied for treatment. In the experimental group, photosensitizer was applied and the method of the present disclosure was used for illumination.

In the experimental group, the puncture needle tubing described in example 4 is used for irradiation laser.

The control groups 1-3 correspond to comparative examples 1-3 in example 8, and the method of laser irradiation thereof is consistent with that of experimental groups.

Method: ten days after treatment, the rats were dissected. And, the coronal incision was made according to the puncture point on the surface of rats. Tumor size was vertically and horizontally measured. tumor volume=$a^2bII/6$ (a is a short diameter of the tumor, and b is a long diameter of the tumor). the tumor growth inhibition rate=[(average volume of tumor in the control group−average volume of the tumor in the experimental group/average volume of the tumor in the control group)]×100%. The obtained inhibition rate of the tumor growth is shown as below.

|  | experimental group | control group1 | control group 2 | control group 3 |
|---|---|---|---|---|
| the inhibition rate of the tumor growth | 86.34% | 65.82% | 61.47% | 52.98% |

Therefore, in the treatment of photodynamic tumor, the efficiency of light emission and illumination has a direct impact on the final treatment effect. The treatment effect of the experimental group is significantly higher than that of the control group.

In the present disclosure, memory metals include but are not limited to nickel-titanium alloy, copper-nickel alloy, copper-aluminum alloy and copper-zinc alloy.

The above description is only a preferred embodiment of the present disclosure, and is not intended to limit the present disclosure. It should be appreciated that various modifications and changes can be made to the present disclosure. Any modifications, equivalents, improvements, etc. made within the spirit and scope of the present disclosure are intended to be included within the scope of the present disclosure.

The invention claimed is:

1. A memory metal optical fiber puncture needle tubing, comprising:
   an optical fiber comprising a body portion and a head portion, the head portion comprising a cylindrical head portion and a tapered head portion, the tapered head portion having a tapered diameter that decreases as a distance away from the cylindrical head portion increases;
   a body tube surrounding the body portion;
   a metal casing wrapped around the cylindrical head portion; and
   a split-shaped needle made of memory metal surrounding a periphery of the tapered head portion,
   wherein
   the metal casing is fixedly connected with the split-shaped needle, and the split-shaped needle is composed of a plurality of tapered petals,
   when a temperature of the split-shaped needle is T0, each of the tapered petals in the split-shaped needle made of memory metal is in a closed state such that the split-shaped needle with the tapered petals in the closed state exhibits a conical structure within which the tapered head portion of optical fiber is accommodated,
   when the temperature of the split-shaped needle is T1, each of the tapered petals in the split-shaped needle made of memory metal is in an opened state such that the tapered head portion of the optical fiber is exposed to enable light to be directly irradiated onto a target, and
   when each of the tapered petals is in the closed state, adjacent sides of two adjacent tapered petals overlap in a radial direction with respect to a central axis of the tapered head portion.

2. The memory metal optical fiber puncture needle tubing according to claim 1, wherein
   the metal casing has an inverted-tooth structure along a length of the metal casing, the inverted-tooth structure having first surface facing a tapered head portion side of the optical fiber and a second surface facing a body portion side of the optical fiber, the first surface being at a first angle with respect to the cylindrical head portion that is less than a second angle of the second surface with respect to the cylindrical head portion so that the metal casing has a smaller resistance when advancing toward the target through a body as compared to a larger resistance that the metal casing has when retreating away from the target through the body, thereby effectively reducing an amount of thrust required for puncturing the body,
   the body tube is a spiral tube comprising a plurality of spiral coils wrapped around the body portion such that the body tube has a spiral structure having spiral kerfs formed by laser and
   a length of the body tube is 1 to 2 m.

3. The memory metal optical fiber puncture needle tubing according to claim 2, wherein
   the metal casing is a spiral structure wrapped around a periphery of the cylindrical head portion of the optical fiber, to integrally connect the optical fiber with the metal casing,
   each of the tapered petals has an arc-shaped surface, and each arc-shaped surface of each tapered has a same curvature as the arc-shaped surface of each other tapered petal at a corresponding point along the central axis of the tapered head portion.

4. The memory metal optical fiber puncture needle tubing according to claim 3, wherein
   the metal casing comprises a metal sheet with a first thickness on a tapered head portion side of the metal sheet and a second thickness on a body portion side of the metal sheet,
   the second thickness of the metal sheet is greater than the first thickness of the metal sheet.

5. The memory metal optical fiber puncture needle tubing according to claim 4, wherein the body portion of the optical fiber is configured to be communicatively coupled with a light source, and the tapered petals of the split-shaped needle are configured to absorb heat from the light source by way of the optical fiber such that light irradiated by the light source increases the temperature of the split-shaped needle from T0 to T1 such that the tapered petals are in the opened state when the temperature of the split-shaped needled is T1.

6. The memory metal optical fiber puncture needle tubing according to claim 1, wherein
   the temperature T0 is 37° C., and the temperature T1 is 50° C.

7. The memory metal optical fiber puncture needle tubing according to claim 4, wherein
   a length of the head portion is 7 to 10 mm, and a length of the split-shaped needle is 2.5 to 4 mm,
   a length of the metal casing is 4.5 to 6 mm,
   the metal casing has at least one kerf having a width of 0.1 to 0.2 mm, and a width of the metal sheet for making the spiral structure of the metal casing is 0.2 to 1 mm, and
   the first thickness of the metal sheet is 50 to 70 μm, the second thickness of the metal sheet is 90 to 110 μm, and a difference between the first thickness and the second thickness is 30 to 50 μm.

8. The memory metal optical fiber puncture needle tubing according to claim 7, wherein
the split-shaped needle comprises a tail end and a tip end, and a width of each tapered petal is gradually decreased from the tail end to the tip end,
when each of tapered petals is closed, a diameter of the tail end is larger than that of the tip end,
the tail ends of the tapered petals are integrally connected to form an annular ring that is fixedly connected to the metal casing, and
when each of tapered petals is in the closed state, the adjacent sides of two adjacent tapered petals are abutted, and the split-shaped needle is a fully enclosed conical structure.

9. The memory metal optical fiber puncture needle tubing according to claim 8, wherein
in the tapered petals, the adjacent sides of the adjacent tapered petals are inclined faces with respect to an inner circumference of the tapered head portion when the tapered petals are in the closed state, and all of the inclined faces of the tapered petals are consistent in direction,
a thickness of the body tube is 0.05 to 0.1 mm, the width of the kerfs for forming the spiral structure of the body tube is 0.02 to 0.2 mm, and a width of a spiral sheet for making the spiral structure of the body tube is 0.5 to 3 mm,
the body tube comprises one or more of stainless steel, synthetic fiber, carbon fiber, titanium alloy, gold, or silver, and
the memory metal optical fiber puncture needle tubing further comprises:
a polymer jacket surrounding the body tube; and
a hydrophilic or hydrophobic coating on the polymer jacket.

10. The memory metal optical fiber puncture needle tubing according to claim 5 wherein
the body portion of the optical fiber is coated with a body coating for preventing light from being emitted from a periphery of the body portion of the optical fiber, and
the tapered head portion of the optical fiber has a refractive index of 1.45 to 1.55 and a taper angle with respect to the central axis of 7° to 25°.

11. The memory metal optical fiber puncture needle tubing according to claim 1, wherein when the tapered petals are in the closed state, the adjacent sides of the adjacent tapered petals are inclined with respect to an inner circumference of the tapered head portion, the adjacent sides of two adjacent tapered petals are abutted, and the split-shaped needle is a fully enclosed conical structure.

* * * * *